United States Patent [19]

Kirschenheuter et al.

[11] Patent Number: 5,281,617
[45] Date of Patent: Jan. 25, 1994

[54] N-SUCCINIMIDYL AND N-PHTHALIMIDYL ESTERS OF 2-PHENYLALKANOIC ACID DERIVATIVES AS INHIBITORS OF HUMAN LEUKOCYTE ELASTASE

[75] Inventors: Gary P. Kirschenheuter, Arvada; John C. Cheronis, Lakewood, both of Colo.

[73] Assignee: Cortech, Inc., Denver, Colo.

[21] Appl. No.: 14,573

[22] Filed: Feb. 5, 1993

[51] Int. Cl.$^5$ .................. A61K 31/40; C07D 207/46; C07D 209/32
[52] U.S. Cl. ..................... 514/417; 514/425; 514/409; 514/414; 548/542; 548/475; 548/407; 548/454
[58] Field of Search ............... 548/454, 542, 475, 407, 548/425; 514/417, 409, 414

[56] References Cited

U.S. PATENT DOCUMENTS 5,039,696  8/1991  Niwata et al. .................. 514/425

Primary Examiner—Mary C. Lee
Assistant Examiner—Joseph K. McKane
Attorney, Agent, or Firm—Cushman, Darby & Cushman

[57] ABSTRACT

N-succinimidyl and N-phthalimidyl esters of phenylalkanoic acid derivatives which are useful as inhibitors of HLE or HNE.

12 Claims, No Drawings

N-SUCCINIMIDYL AND N-PHTHALIMIDYL ESTERS OF 2-PHENYLALKANOIC ACID DERIVATIVES AS INHIBITORS OF HUMAN LEUKOCYTE ELASTASE

The present invention relates to certain 2-arylalkanoate esters which are useful as inhibitors of human leukocyte elastase (HLE) or equivalently human neutrophil elastase (HNE).

RELATED APPLICATION

This application is related to the commonly assigned U.S. application Ser. No. 07/528,967, filed May 22, 1990, now U.S. Pat. No. 5,214,191.

BACKGROUND OF THE INVENTION

There has been considerable research effort in recent years toward the development of HLE (or HNE) inhibitors because it appears that HLE may be responsible for a variety of human diseases. Tests have shown that there is an apparent association between HLE and emphysema. See, for example, Sandbero et al., *The New England Journal of Medicine*, 304:566 (1981). Other diseases and medical problems, such as arthritis and related inflammatory conditions, dermatitis and ischemia/reperfusion injury have also been associated with HLE. See, Dinerman et al., *JACC*, Vol. 15, No. 7, June 1990: 1559-63. Accordingly, there is a need for compounds which are effective inhibitors of HLE or HNE.

Typical prior efforts to deal with elastase inhibition are disclosed in the patent literature, for instance, U.S. Pat. Nos. 4,683,241 and 4,801,610.

SUMMARY OF THE INVENTION

The principal object of the present invention is to provide certain new compounds which are useful as elastase inhibitors. These compounds are characterized by their relatively low molecular weight and high selectivity with respect to HLE. As a consequence, they can be used to prevent, alleviate or otherwise treat disease characterized by the degradation effects caused by HLE on connective tissues in mammals, including humans.

The compounds of the invention may be structurally illustrated by the following formulae (I and II):

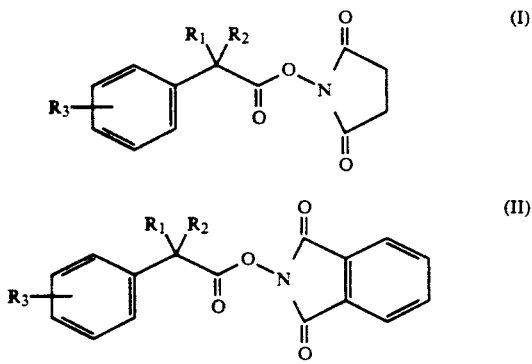

wherein:
$R_1$ and $R_2$, which may be the same or different, are selected from the group consisting of:
hydrogen, alkyl of 1-6 carbons, cycloalkyl of 3 to 6 carbons or together represent a methylene group $-(CH_2)_n-$ where n is a whole number from 1 to 5; provided that both $R_1$ and $R_2$ are not hydrogen;
$R_3$ represents one or more substituents up to five selected from the group consisting of:
hydrogen, halogen, haloalkyl of 1-12 carbons (e.g., $CF_3$), nitro, alkyl of 1-12 carbons, alkoxy of 1-12 carbons, cycloalkyl of 3-12 carbons, alkenyl of 2 to 12 carbons, mono- or dicyclic aryl (e.g., optionally substituted phenyl or naphthyl) or a substituent joining adjacent carbons of the phenyl ring, e.g., $-OCH_2O-$ or $-(CH_2)-_n$, which may be optionally substituted by lower alkyl or by lower alkoxy, where n is a whole number from 1 to 5.

According to the invention, the phenyl may be unsubstituted (i.e., $R_3$ may be hydrogen). However, it is preferred that $R_3$ be other than hydrogen.

It will be appreciated that when $R_1$ and $R_2$ are different, the carbon atom to which these substituents are attached (i.e., the "alpha carbon") is a chiral center and the resulting compounds may exist in enantiomerically pure form or as racemic mixtures of the enantiomers. The invention contemplates such mixtures (+/−) as well as the separate (+ or −) enantiomers thereof.

PREFERRED EMBODIMENTS OF THE INVENTION

Particularly advantageous for present purposes are the compounds of formula (I) where one of $R_1$ and $R_2$ is hydrogen and the other is alkyl, particularly ethyl; and $R_3$ is hydrogen, lower alkyl, cycloalkyl, lower alkoxy, phenyl or the atoms necessary to complete an optionally substituted ring with the adjacent phenyl. The optional substitution in the case of $R_3$ may be, for example, lower alkyl or lower alkoxy, it being understood that reference herein to lower alkyl or lower alkoxy contemplates up to 6 carbon atoms.

As a further feature of the invention, it has been found that compounds which have been modified so as to remove the chiral center at the alpha carbon, i.e., by making $R_1$ and $R_2$ the same, e.g. either methyl or ethyl, or by merging $R_1$ and $R_2$ into a cycloalkyl ring (such as cyclopropyl, cyclobutyl, cyclopentyl or cyclohexyl) are particularly advantageous for use as human neutrophil elastase inhibitors.

Representative compounds according to the invention are shown in Tables I and II.

TABLE I

This table exemplifies compounds of the formula (I) wherein $R_1$-$R_3$ have the values indicated. Positioning of the substituents represented by $R_3$ is specified numerically, the link of the phenyl ring to the rest of the molecule being the 1-position.

| Compound No. | $R_1$ | $R_2$ | $R_3$ |
|---|---|---|---|
| (±)-1 | H | $C_2H_5$ | H |
| (−)-2 | H | $C_2H_5$ | H |

-continued

| Compound No. | $R_1$ | $R_2$ | $R_3$ |
|---|---|---|---|
| (+)-3 | H | $C_2H_5$ | H |
| 4 | H | $CH_3$ | H |
| 5 | H | n-$C_3H_7$ | H |
| 6 | H | i-$C_3H_7$ | H |
| 7 | H | n-$C_4H_9$ | H |
| 8 | H | $CH_3$ | 3-$CF_3$ |
| 9 | H | $C_2H_5$ | 3-$CF_3$ |
| 10 | H | n-$C_3H_7$ | 3-$CF_3$ |
| 11 | H | i-$C_3H_7$ | 3-$CF_3$ |
| 12 | | $(CH_2)_3$ | H |
| 13 | | $(CH_2)_4$ | H |
| 14 | H | $C_2H_5$ | 2-$CF_3$ |
| 15 | H | $CH_3$ | 4-$CF_3$ |
| 16 | H | $C_2H_5$ | 4-$CF_3$ |
| 17 | H | $CH_3$ | 4-(2-$CH_3$-1-$C_3H_6$) |
| 18 | H | $C_2H_5$ | 4-(2-$CH_3$-2-$C_3H_6$) |
| 19 | $C_2H_5$ | $C_2H_5$ | H |
| 20 | H | $C_2H_5$ | 2-$OCH_3$ |
| 21 | H | $C_2H_5$ | 3-$OCH_3$ |
| 22 | H | $C_2H_5$ | 4-$OCH_3$ |
| (+)-23 | H | $CH_3$ | 3,4-(—CHCHC($OCH_3$)CH—) |
| 24 | H | $CH_3$ | 4-$NO_2$ |
| 25 | H | $CH_3$ | 4-F |
| 26 | | $(CH_2)_2$ | H |
| 27 | H | —$CH_2C(O)CH_3$ | H |
| 28 | H | i-$C_3H_7$ | 2-$CH_3$ |
| 29 | H | $C_2H_5$ | 3,4-(—$OCH_2O$—) |
| 30 | H | $C_2H_5$ | 3,4,5-tri-$OCH_3$ |
| 31 | H | $C_2H_5$ | 4-$OC_2H_5$ |
| 32 | H | $C_2H_5$ | 4-O-n-$C_4H_9$ |
| 33 | H | $C_2H_5$ | 3,4-(—CHCHC($OCH_3$)CH—) |
| 34 | H | $CH_3$ | 3,4-(—CHCHC($OCH_3$)CH—) |
| 35 | H | —$CH_2CH(CH_3)_2$ | H |

TABLE II

This table exemplifies compounds of the formula (II) wherein $R_1$-$R_3$ have the values indicated.

| Compound No. | $R_1$ | $R_2$ | $R_3$ |
|---|---|---|---|
| (±)-36 | H | $C_2H_5$ | H |
| (R)-(−)-37 | H | $C_2H_5$ | H |
| (S)-(+)-38 | H | $C_2H_5$ | H |

Broadly described, the products of the invention may be prepared by procedures available to those skilled in the art. A representative synthesis procedure may be illustrated by the following Reaction Scheme A:

REACTION SCHEME A

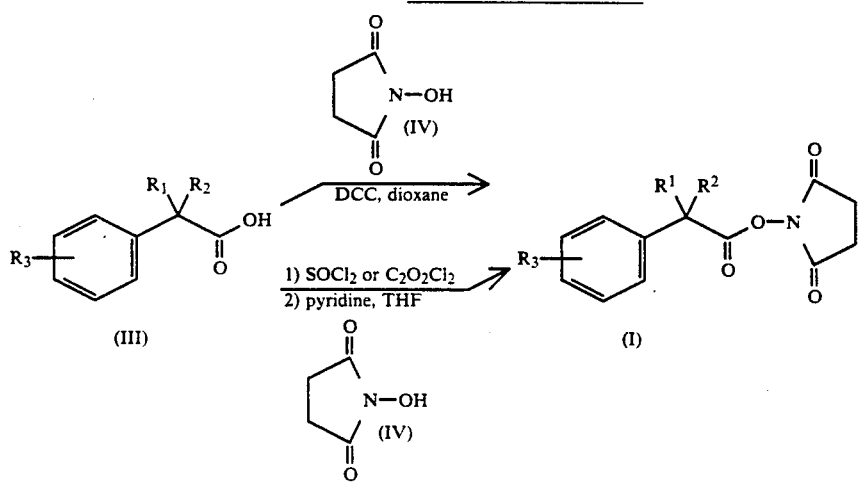

REACTION SCHEME A —continued

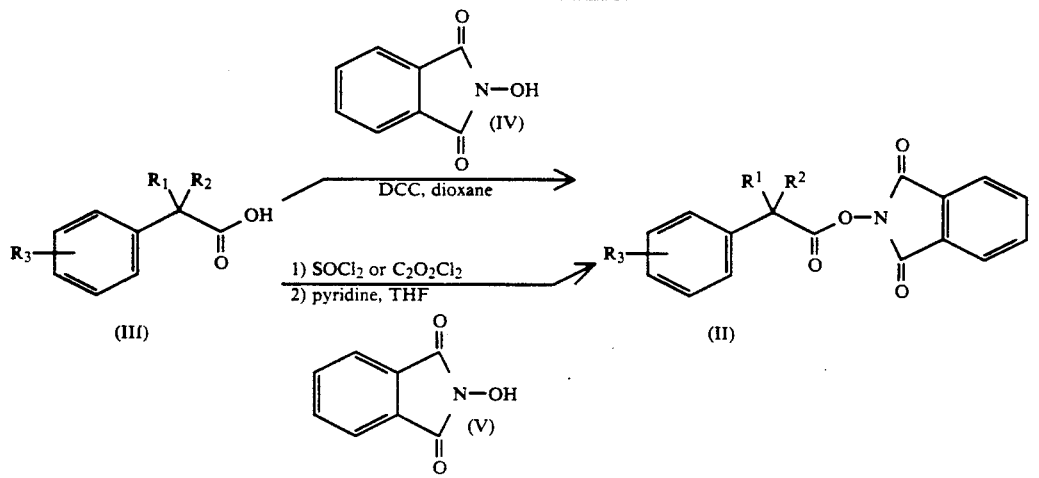

The compounds of the invention may be prepared by esterification of the 2-phenylalkanoic acid derivatives (III) with N-hydroxysuccinimide (IV) or N-hydroxyphthalmide (V) in the presence of dicyclohexylcarbodimide (DCC) in dioxane to give the desired esters (I) and (II), respectively. Alternatively, one may convert the acids (III) to the corresponding acid chlorides by treatment with thionyl chloride or oxalyl chloride. Reaction of these acid chlorides with (IV) or (V) in the presence of organic bases such as pyridine affords the esters (I) and (II). It will be evident to those skilled in the art that each of the aforementioned reactions may require slightly different conditions, depending on the reactants involved, to obtain the best yields of the desired products. There are additional general methods of synthesizing the compounds of the invention available to those skilled in the field of chemistry.

The following examples are given to illustrate the preparation of specific compounds according to the invention:

EXAMPLE 1

(±-2-Phenylbutanoyloxysuccinimide (1)

A solution of dicyclohexylcarbodiimide (6.91 g, 0.033 mol) in 33 mL of dry dioxane was added to a solution of 2-phenylbutyric acid (5.00 g, 0.030 mol) and N-hydroxysuccinimide (3.86 g, 0.034 mol) and the resulting mixture was allowed to stir overnight. The precipitated dicyclohexylurea by-product was filtered off and the filtrate concentrated under vacuum. The residue was dissolved in 5 mL of methylene chloride and filtered to remove a small amount of additional urea by-product. The solution was evaporated to give a white solid which was recrystallized from methanol to give 5.17 g (65%) of the product as white crystals; mp 96.5°–97.5° C.; $^1$H NMR (CDCl$_3$) δ 0.99 (t, 3 H, J=7.4 Hz), 1.85–2.00 (m, 1 H), 2.13–2.28 (m, 1 H), 2.72 (br s, 4 H), 3.78 (t, 1 H, J=7.6 Hz), 7.35 (s, 5 H); $^{13}$C NMR (CDCl$_3$) δ 11.49, 25.30, 26.89, 50.25, 127.95, 128.18, 128.92, 136.90, 169.24, 169.62; Anal. Calcd for C$_{14}$H$_{15}$NO$_4$: C, 64.36; H, 5.79; N, 5.36. Found: C, 64.63; H, 5.84; N, 5.34.

The compounds described in Examples 2–32 were prepared according to the procedure utilized in Example 1.

EXAMPLE 2

(R)-(−)-2-Phenylbutanoyloxysuccinimide (2)

yield 65%; $α_D$ = −47.08°.

EXAMPLE 3

(S)-(+)-2-Phenylbutanoyloxysuccinimide (3)

yield 65%; $α_D$ = +47.99°.

EXAMPLE 4

(±)-2-Phenylpropanoyloxysuccinimide (4)

yield 83%; mp 69°–70° C.; $^1$H NMR (CDCl$_3$) δ 1.64 (d, 3 H, J=7.2 Hz), 2.78 (br s, 4 H), 4.05 (q, 1 H, J=7.2 Hz), 7.30–7.41 (m, 5 H, ArH); $^{13}$C NMR (CDCl$_3$) 18.68, 25.34, 42.78, 127.72, 127.94, 129.04, 138.43, 169.25, 170.14; Anal. Calcd for C$_{13}$H$_{13}$N$_4$: C, 63.15; H, 5.30; N, 5.66. Found: C, 62.73; H, 5.30; N, 5.20.

EXAMPLE 5

(±)-2-Phenylpentanoyloxysuccinimide (5)

yield 77%; mp 84°–85° C.; $^1$H NMR (CDCl$_3$) δ 0.94 (t, 3 H, J=7.4 Hz), 1.25–1.50 (m, 2 H), 1.80–1.95 (m, 1 H), 2.08–2.23 (m, 1 H), 2.76 (br s, 4 H), 3.88 (t, 1 H, J=7.6 Hz), 7.28–7.43 (m, 5 H, ArH); $^{13}$C NMR (CDCl$_3$) δ 13.38, 20.13, 25.32, 35.62, 48.34, 127.95, 128.17, 137.08, 169.22, 169.74; Anal. Calcd for C$_{15}$H$_{17}$NO$_4$: C, 65.44; H, 6.22; N, 5.09. Found: C, 5.20; H, 6.22; N, 4.98.

EXAMPLE 6

(±)-3-Methyl-2-phenylbutanoyloxysuccinimide (6)

yield 19%; mp 130.5°–132.0° C.; $^1$H NMR (CDCl$_3$) δ 0.08 (d, 3 H, J=6.6 Hz), 1.17 (d, 3 H, J=6.6 Hz), 2.40 (d(7), 1 H, J=6.6 Hz, J=9.6 Hz), 2.76 (br s, 4 H), 3.50 (d, 1 H, J=9.6 Hz), 7.20–7.40 (m, 5H, ArH); $^{13}$C NMR (CDCl$_3$ δ 19.85, 20.83, 25.30, 2.16, 56.40, 128.03, 128.75, 128.84, 136.07, 169.24, 169.44, 177.40; Anal. Calcd for C$_{15}$H$_{17}$NO$_4$: C, 65.44; H, 6.22; N, 5.09. Found: C, 65.23; H, 6.24; N, 5.11.

EXAMPLE 7

(±)-2-Phenylhexanoyloxysuccinimide (7)

yield 18%; mp 49°–50° C.; $^1$H NMR (CDCl$_3$) δ 0.90 (t, 3 H, J=7.0 Hz), 1.27–1.46 (m, 4 H), 1.85–1.98 (m, 1

H), 2.12–2.27 (m, 1 H), 2.79 (br s, 4 H), 3.87 (t, 1 H, J=7.7 Hz), 7.28–7.45 (m, 5 H, ArH); $^{13}$C NMR (CDCl$_3$) δ 13.50, 22.05, 25.34, 29.04, 33.28, 48.59, 127.95, 128.17, 128.97, 137.12, 169.25, 169.77; Anal. Calcd for C$_{16}$H$_{19}$NO$_4$: C, 66.42; H, 6.62; N, 4.84. Found: C, 65.94; H, 6.90; N, 5.24.

EXAMPLE 8

(±)-2-(3'-Trifluoromethylphenyl)propanoyloxysuccinimide (8)

yield 12%; mp 99°–99.5° C.; $^1$H NMR (CDCl$_3$) δ 1.66 (d, 3 H, J=7.2 Hz), 2.79 (br s, 4 H), 4.12 (q, 1 H, J=7.2 Hz), 7.49–7.71 (m, 4 H, ArH); $^{13}$C NMR (CDCl$_3$) δ 18.83, 25.46, 42.63, 123.84 (1, $^1J_{CF}$=270.8 Hz), 124.49 (q, $^3J_{CF}$=3.9 Hz), 124.67 (q, $^3J_{CF}$=3.5 Hz), 129.35, 130.97, 131.10 (q, $^2J_{CF}$=32.2 Hz), 139.09, 168.88, 169.21.

EXAMPLE 9

(±)-2-(3'-Trifluoromethylphenyl)butanoyloxysuccinimide (9)

yield 11%; mp 80.5°–81.5° C.; $^1$H NMR (CDCl$_3$) δ 1.01 (t, 3 H, J=7.4 Hz), 1.87–2.02 (m, 1 H), 2.16–2.31 (m, 1 H), 2.79 (br s, 4 H), 3.86 (t, 1 H, J=7.6 Hz), 7.46–7.63 (m, 4 H, ArH); $^{13}$C NMR (CDCl$_3$) δ 11.68, 25.48, 27.21, 50.06, 123.86 (q, $^1J_{CF}$=2.70 Hz), 124.73 (q, $^3J_{CF}$=3.7 Hz), 124.93 (q, $^3J_{CF}$=3.3 Hz), 129.28, 131.40 (q, $^2J_{CF}$=32.2 Hz), 137.62, 168.77, 168.86; Anal. Calcd for C$_{15}$H$_{14}$F$_3$NO$_4$: C, 54.72; H, 4.29; N, 4.25; F, 17.31. Found: C, 54.82; H, 4.18; N, 4.25; F, 15.75.

EXAMPLE 10

(±)-2-(3'-Trifluoromethylphenyl)pentanoyloxysuccinimide (10)

yield 5%; mp 76°–77° C.; $^1$H NMR (CDCl$_3$) δ 0.96 (t, 3 H, J=7.5 Hz), 1.30–1.50 (m 2 H), 1.80–1.95 (m, 1 H), 2.12–2.27 (m, 1 H), 2.80 (br s, 4 H), 3.96 (t, 1 H, J=7.8 Hz), 7.48–7.67 (m, 4 H, ArH); Anal. Calcd for C$_{16}$H$_{16}$F$_3$NO$_4$: C, 55.98; H, 4.70; N, 4.08; F, 16.60. Found: C, 56.58; H, 4.77; N, 4.13; F, 16.27.

EXAMPLE 11

(±)-3-Methyl-2-(3'-Trifluoromethylphenyl)-butanoyloxysuccinimide (11)

yield 9%; mp 114°–115° C.; $^1$H NMR (CDCl$_3$) δ 0.81 (d, 3 H, J=6.7 Hz), 1.19 (d, 3 H, J=6.5 Hz), 2.41 (dqq, J=6.5 Hz, J=6.7 Hz, J=9.8 Hz), 2.78 (br s, 4 H), 3.59 (d, 1 H, J=9.8 Hz), 7.45–7.63 (m, 4 H, ArH); $^{13}$C NMR (CDCl$_3$) δ 19.95, 20.89, 5.48, 35.56, 56.08, 123.86 (q, $^1J_{CF}$=270.9 Hz), 124.80 (q, $^3J_{CF}$=3.7 Hz), 125.38 (q, $^3J_{CF}$=3.5 Hz), 29.16, 130.93 (q, $^2J_{CF}$=32.2 Hz), 131.92, 136.79, 168.59, 168.84; Anal. Calcd for C$_{16}$H$_{16}$F$_3$NO$_4$: C, 55.98; H, 4.70; N, 4.08; F, 16.60. Found: C, 56.44; H, 4.75; N, 4.17; F, 16.27.

EXAMPLE 12

1-Phenylcyclobutanecarboxyoxysuccinimide (12)

yield 49%; mp 123.5°–124.5° C.; $^1$H NMR (CDCl$_3$) δ 1.92–2.06 (m, 1 H), 2.15–2.30 (m, 1 H), 2.60–2.75 (m, 2 H), 2.76 (br s, 4 H), 2.97–3.09 (m. 2 H), 7.25–7.42 (m, 5 H, ArH); $^{13}$C NMR (CDCl$_3$) δ 16.47, 25.35, 32.42, 50.72, 126.51, 127.51, 128.74, 141.24, 169.31, 171.58; Anal. Calcd for C$_{15}$H$_{17}$NO$_4$: C, 65.92; H, 5.53; N, 5.13. Found: C, 65.37; H, 5.56; N, 4.99.

EXAMPLE 13

1-Phenylcyclopentanecarboxyloxysuccinimide (13)

yield 98%; mp 131°–132° C.; $^1$H NMR (CDCl$_3$) δ 1.78–1.98 (m, 4 H), 2.05–2.18 (m, 2 H), 2.65–2.85 (br s, m, 6 H), 7.25–7.55 (m, 5 H, ArH); $^{13}$C NMR (CDCl$_3$) δ 23.58, 25.32, 36.90, 57.81, 126.90, 127.54, 128.70, 141.27, 169.33, 171.98; Anal. Calcd for C$_{16}$H$_{17}$NO$_4$: C, 66.98; H, 5.96; N, 4.88. Found: C, 66.57; H, 6.05; N, 4.45.

EXAMPLE 14

(±)-2-(2'-Trifluoromethylphenyl)butanoyloxysuccinimide (14)

$^1$H NMR (CDCl$_3$ δ 1.01 (t, 3 H, J=6.9 Hz), 1.88–2.03 (m, 1 H), 2.16–2.31 (m, 1 H), 2.79 (br s, 4 H), 4.27 (t, 1 H, J=7.5 Hz), 7.25–7.72 (m, 4 H, ArH).

EXAMPLE 15

(±)-2-(4'-Trifluoromethylphenyl)propanoyloxysuccinimide (15)

$^1$H NMR (CDCl$_3$) δ 1.66 (d, 3 H, J=7.2 Hz), 2.82 (br s, 4 H), 4.12 (q, 1 H, J=7.2 Hz), 7.50 (d, 1 H, J=8.4 Hz), 7.65 (d, 2 H, J=8.4 Hz).

EXAMPLE 16

±)-2-(4'-Trifluoromethylphenyl)butanoyloxysuccinimide (16)

$^1$H NMR (CDCl$_3$) δ 1.00 (t, 3 H, J=7.5 Hz), 1.86–2.01 (m, 1 H), 2.16–2.31 (m, 1 H), 2.80 (br s, 4 H), 3.86 (t, 1 H, J=7.5 Hz), 7.49 (d, 2 H, J=8.1 Hz), 7.64 (d, 2 H, J=8.4 Hz).

EXAMPLE 17

(±)-2-(4'-(2-Methylpropyl)phenyl)propanoyloxysuccinimide (17)

yield 70%; mp 94°–95° C.; $^1$H NMR (CDCl$_3$) δ 0.90 (d, 6 H, J=6.6 Hz), 1.62 (d, 3 H, J=7.2 Hz), 1.88–1.94 (m, 1 H), 2.46 (d, 2 H, J=6.6 Hz), 2.78 (br s, 4 H), 4.03 (q, 1 H, J=7.2 Hz), 7.14 (d, 2 H, J=8.1 Hz), 7.26 (d, 2 H, J=8.1 Hz); $^{13}$C NMR (CDCl$_3$) δ 18.72, 22.13, 25.33, 29.91, 42.37, 44.87, 127.38, 129.72, 135.61, 141.44, 169.32, 170.32; Anal. Calcd for C$_{17}$H$_{21}$NO$_4$: C, 67.31; H, 6.98; N, 4.62. Found: C, 67.01; H, 6.97; N, 4.56.

EXAMPLE 18

(±)-2-(4'-(2-Methylpropyl)phenyl)butanoyloxysuccinimide (18)

yield 67%; mp 95°–96° C.; $^1$H NMR (CDCl$_3$) δ 0.89 (d, 6 H, J=6.6 Hz), 0.99 (t, 3 H, J=7.4 Hz), 1.80–1.98 (m, 2 H), 2.12–2.27 (m, 1 H), 2.46 (d, 2 H, J=6.6 Hz), 2.78 (br s, 4 H), 3.76 (t, 3 H, J=7.5 Hz), 7.13 (d, 2 H, J=8.1 Hz), 7.25 (d, 2 H, J=8.1 Hz); $^{13}$C NMR (CDCl$_3$) δ 11.59, 22.14, 25.34, 29.96, 29.92, 44.88, 49.90, 127.86, 129.65, 131.09, 141.49, 169.31, 169.34, 169.84; Anal. Calcd for C$_{18}$H$_{23}$NO$_4$: C, 68.12; H, 7.30; N, 4.41. Found: C, 68.07; H, 7.41; N, 4.30.

EXAMPLE 19

2-Ethyl-2-phenylbutanoyloxysuccinimide (19)

yield 29%; $^1$H NMR (CDCl$_3$) δ 0.87 (t, 6 H, J=7.5 Hz), 2.16 (q, 2 H, J=7.5 Hz), 2.17 (q, 2 H, J=7.5 Hz), 2.69–2.91 (br m, 4 H), 7.26–7.41 (m, 5 H); $^{13}$C NMR (CDCl$_3$) δ 7.91, 25.38, 25.56, 27.52, 54.58, 127.23, 127.38, 128.48, 140.43, 169.46, 171.84; Anal. Calcd for $C_{16}H_{19}NO_4$: C, 66.42; H, 6.62; N, 4.84. Found: C, 65.90; H, 6.66; N, 4.93.

EXAMPLE 20

(±)-2-(2′-Methoxyphenyl)butanoyloxysuccinimide (20)

yield 63%; $^1$H NMR (CDCl$_3$) δ 0.99 (t, 3 H, J=7.4 Hz), 1.85–2.00 (m, 1 H), 2.08–2.23 (m, 1 H), 2.77–2.84 (br s, 4 H), 3.85 (s, 3 H), 4.14 (t, 1 H, J=7.5 Hz), 6.87–7.00 (m, 2 H), 7.24–7.32 (m, 2 H); $^{13}$C NMR (CDCl$_3$) 11.56, 24.72, 25.35, 43.96, 55.31, 110.64, 120.70, 125.51, 128.90, 129.01, 157.17, 169.38, 170.10.

EXAMPLE 21

(±)-2-(3′-Methoxyphenyl)butanoyloxysuccinimide (21)

yield 42%; $^1$H NMR (CDCl$_3$) δ 1.00 (t, 3 H, J=7.4 Hz), 1.84–1.99 (m, 1 H), 2.11–2.26 (m, 1 H), 2.79 (br s, 4 H), 3.76 (t, 1 H, J=7.7 Hz), 3.82 (s, 3 H), 6.81–6.95 (m, 3 H), 7.20–7.33 (m, 1 H); $^{13}$C NMR (CDCl$_3$ 11.56, 25.33, 26.88, 50.26, 55.12, 113.55, 113.59, 120.52, 129.89, 138.33, 160.11, 169.38, 169.55; Anal. Calcd for $C_{15}H_{17}NO_5$: C, 61.85; H, 5.88; N, 4.81. Found: C, 61.55; H, 6.15; N, 4.75.

EXAMPLE 22

(±)-2-(4′-Methoxyphenyl)butanoyloxysuccinimide (22)

yield 87%; mp 94°–95° C.; $^1$H NMR (CDCl$_3$) δ 0.98 (t, 3 H, J=7.4 Hz), 1.80–1.95 (m, 1 H), 2.09–2.24 (m, 1 H), 2.75 (br s, 4 H), 3.73 (t, 1 H, J=7.6 Hz), 3.79 (s, 3 H), 6.89 (d, 2 H, J=8.7 Hz), 7.26 (d, 2 H, J=8.7 Hz); $^{13}$C NMR (CDCl$_3$) δ 11.48, 25.28, 26.87, 49.37, 44.07, 114.23, 128.84, 129.22, 159.37, 169.32, 169.84; Anal. Calcd for $C_{15}H_{17}NO_5$: C, 61.85; H, 5.88; N, 4.81. Found: C, 61.75; H, 5.98; N, 4.63.

EXAMPLE 23

(±)-2-(6′-Methoxynaphthyl)propanoyloxysuccinimide (23)

yield 46%; $^1$H NMR (CDCl$_3$) δ 1.70 (d, 3 H, J=7.2 Hz), 2.74 (br s, 4 H), 3.90 (s, 3 H), 4.18 (q, 1 H, J=7.2 Hz), 7.11–7.17 (m, 2 H), 7.43 (d, 1 H, J=8.7 Hz), 7.73 (d, 1 H, J=8.7 Hz), 7.74–7.77 (m, 2 H); $^{13}$C NMR (CDCl$_3$ δ 18.68, 25.31, 42.73, 55.19, 105.69, 119.31, 126.03, 126.50, 127.65, 129.04, 129.55, 133.48, 134.14, 158.15, 169.30, 170.27; Anal. Calcd for $C_{18}H_{17}NO_5$: C, 66.05; H, 5.23; N, 4.28.

EXAMPLE 24

(±)-2-(4′-Nitrophenyl)propanoyloxysuccinimide (24)

yield 27%; $^1$H NMR (CDCl$_3$) δ 1.68 (d, 3 H, J=7.2 Hz), 2.83 (br s, 4 H), 4.18 (q, 1 H, J=7.2 Hz), 7.56 (d, 2 H, J=7.5 Hz), 8.24 (d, 2 H, J=7.5 Hz); $^{13}$C NMR (CDCl$_3$) δ 18.48, 25.33, 42.61, 124.25, 128.85, 145.48, 147.77, 169.06; Anal. Calcd for $C_{13}H_{12}N_2O_6$: C, 53.43; H, 4.14; N, 9.59. Found: C, 53.12; H, 4.43; N, 9.38.

EXAMPLE 25

(±)-2-(4′-Fluorophenyl)propanoyloxysuccinimide (25)

yield 48%; $^1$H NMR (CDCl$_3$) δ 1.59 (d, 3 H, J=7.2 Hz), 2.72 (br s, 4 H), 4.03 (q, 1 H, J=7.2 Hz), 7.04 (dd, 2 H $J_{HF}$=7.5 Hz, $J_{HF}$=8.7 Hz), 7.33 (dd, 2 H, $J_{HH}$=7.5 Hz, $J_{HF}$=5.4 Hz); $^{13}$C NMR (CDCl$_3$) δ 18.44, 25.08, 41.75, 115.62 (d, $^2J_{CF}$=21.7 Hz), 129.27 (d, $^3J_{CF}$=8.4 Hz), 134.09 (d, $^4J_{CF}$=3.3 Hz), 162.30 (d, $^1J_{CF}$=247.3 Hz), 169.35, 169.88: Anal. Calcd for $C_{13}H_{12}FNO_4$: C, 58.87; H, 4.56; N, 5.28; F, 7.16. Found: C, 59.29; H, 4.51; N, 5.27; F, 7.23.

EXAMPLE 26

1-Phenylcyclopropanecarboxyloxysuccinimide (26)

yield 63%; mp 133.5°–134.5° C.; $^1$H NMR (CDCl$_3$) δ 1.40–1.48 (m, 2 H), 1.80–1.88 (m, 2 H), 2.66 (br s, 4 H), 7.24–7.47 (m, 5 H, ArH); $^{13}$C NMR (CDCl$_3$) δ 18.19, 25.11, 26.86, 127.92, 128.42, 130.56, 136.93, 169.35, 170.25; Anal. Calcd for $C_{14}H_{13}NO_4$: C, 64.86; H, 5.05; N, 5.40. Found: C, 64.50; H, 5.18; N, 5.33.

EXAMPLE 27

(±)-2-Phenyllevulinyloxysuccinimide (27)

yield 76%; $^1$H NMR (CDCl$_3$ δ 2.16 (s, 3 H), 2.76 (br s, 4 H), 2.92 (dd, 1 H J=5.4 Hz, J=18.3 Hz), 3.37 (dd, 1 H, J=9.0 Hz, J=18.3 Hz), 4.47 (dd, 1 H, J=5.4 H, J=9.0 Hz), 7.27–7.40 (m, 5 H ArH); $^{13}$C NMR (CDCl$_3$ δ 25.28, 29.53, 43.49, 46.89, 128.10, 128.23, 129.16, 136.06, 169.06, 169.19, 204.93,; Anal. Calcd for $C_{15}H_{15}NO_5$: C, 62.28; H, 5.23; N, 4.84. Found: C, 62.38; H, 5.32; N, 4.81.

EXAMPLE 28

(±)-2-(2′-Methylphenyl)-3-methylbutanoyloxysuccinimide (28)

$^1$H NMR (CDCl$_3$ δ 0.80 (d, 3 H, J=6.6. Hz), 1.22 (d,3 H, J=6.6 Hz), 2.42 (s, 3 H), 2.35–2.54 (m, 1 H), 2.79 br s, 4 H), 3.82 (d, 1 H, J=10.5 Hz), 7.18–7.27 (m, 3 H), 7.41 (d, 1 H, J=6.6 Hz); $^{13}$C NMR (CDCl$_3$) δ 19.65, 19.85, 20.99, 25.37, 32.06, 51.31, 126.75, 127.48, 127.75, 130.82, 134.75, 136.89, 169.33, 169.68.

EXAMPLE 29

(±)-2-(3′,4′-Methylenedioxyphenyl)butanoyloxysuccinimide (29)

yield 92%; $^1$H NMR (CDCl$_3$) δ 0.98 (t, 3 H, J=7.4 Hz), 1.80–1.95 (m, 1 H), 2.09–2.24 (m, 1 H), 2.79 (br s, 4 H), 3.69 (t, 1 H, J=7.6 Hz), 5.96 (s, 2 H), 6.79 (s, 2 H), 6.86 (s, 1 H); $^{13}$C NMR (CDCl$_3$) δ 11.48, 25.34, 26.96, 49.86, 101.23, 108.34, 108.48, 121.75, 130.44, 147.47, 148.23, 169.25, 169.67; Anal. Calcd for $C_{15}H_{15}NO_6$: C, 59.01; H, 4.95; N, 4.59. Found: C, 59.06; H, 5.03; N, 4.51.

EXAMPLE 30

(±)-2(3′,4′,5′-Trimethoxyphenol)butanoyloxysuccinimide (30)

yield 85%; $^1$H NMR (CDCl$_3$) δ 1.03 (t, 3 H, J=7.4 Hz), 2.83–2.98 (m, 1 H), 2.10–2.25 (m, 1 H), 2.8 (br s, 4 H), 3.73 (t, 1 H, J=7.6 Hz), 3.85 (s, 3 H), 3.88 (s, 6 H), 6.57 (s, 2 H); $^{13}$C NMR (CDCl$_3$) δ 11.58, 25.33, 27.02, 50.49, 56.00, 60.68, 105.05, 132.53, 137.62, 153.58, 169.25, 169.49. Anal. Calcd for $C_{17}H_{21}NO_7$: C, 58.11; H, 6.02; N, 3.99. Found: C, 58.17; H, 60.07; N, 3.99.

EXAMPLE 31

(±)-2-(4′-Ethoxyphenyl)butanoyloxysuccinimide (31)

yield 99%; $^1$H NMR (CDCl$_3$) δ 0.98 (t, 3 H, J=7.4 Hz), 1.40 (t, 3 H, J=7.0 Hz), 1.80–1.95 (m, 1 H), 2.10–2.25 (m, 1 H), 2.76 (br s, 4 H), 3.72 (t, 1 H, J=7.6 Hz), 4.02 (q, 2 H, J=7.0 Hz), 6.88 d, 2 H, J=8.7 Hz), 7.25 (d, 2 H, J=8.7 Hz); $^{13}$C NMR (CDCl$_3$) δ 6 11.49, 14.54, 25.31, 26.90, 49.42, 63.29, 114.79, 128.68, 129.21, 158.80, 169.31, 169.88; Anal. Calcd for $C_{16}H_{19}NO_5$: C, 62.94; H, 6.27; N, 4.59. Found: C, 62.81; H, 6.21; N, 4.54.

EXAMPLE 32

(±2-(4'-n-Butoxyphenyl)butanoyloxysuccinimide (32)

yield 99%; $^1$H NMR (CDCl$_3$) δ 0.97 (t, 3 H, J=7.4 Hz), 0.98 (t, 3 H, J=7.4 Hz), 1.40–1.57 (m, 2 H), 1.70–1.83 (m, 2 H), 1.80–1.95 (m, 1 H), 2.09–2.59 (m, 1 H), 2.78 (br s, 4 H), 3.72 (t, 1 H, J=7.6 Hz), 3.95 (t, 2 H, J=6.5 Hz), 6.88 d, (2 H, J=8.6 Hz), 7.25 (d, 2 H, J=8.7 Hz); $^{13}$C NMR (CDCl$_3$) δ 11.52, 13.57, 18.99, 25.34, 26.93, 31.11, 49.45, 67.57, 114.82, 128.61, 129.20, 159.03, 169.31, 169.90; Anal. Calcd for C$_{18}$H$_{23}$NO$_5$: C, 64.85; H, 6.95; N, 4.20. Found: C, 64.66; H, 6.93; N, 4.11.

EXAMPLE 33

(±)-2-(6'-Methoxynaphthyl)butanoyloxysuccinimide (33)

A mixture of 2-(6'methoxynaphthyl)butyric acid (0.519 g, 2.12 mmol) in 20 mL of dry methylene chloride was treated with 3.19 mL of a 2.0 thionyl chloride (6.37 mmol) solution and the resulting solution was allowed to stir overnight. The volatile solvents were removed under vacuum to give the crude acid chloride which was used without further purification. A portion of the acid chloride (139 mg, 0.53 mmol) in 10 mL of dry toluene was added to a stirred solution of N-hydroxysuccinimide (61 mg, 0.53 mmol) and pyridine (42 mg, 0.53 mmol) in 10 mL of dry THF. After stirring overnight, the precipitated pyridine hydrochloride was filtered off and the filtrate concentrated under vacuum. The residue was chromotographed on silica gel (CHCl$_3$/MeOH) to afford 15 mg of the product as a white solid. Yield 8%; $^1$H NMR (CDCl$_3$) δ 1.02 (t, 3 H, J=7.4 Hz), 1.95–2.10 (m, 1 H), 2.20–2.35 (m, 1 H), 2.75 (br s, 4 H), 3.91 (m, 4 H), 7.10–7.20 (m, 2 H), 7.40–7.48 (m, 1 H), 7.69–7.82 (m, 3 H); $^{13}$C NMR (CDCl$_3$) δ 11.61, 25.34, 26.90, 50.26, 55.23, 105.70, 119.27, 126.31, 127.25, 127.60, 129.04, 129.57, 131.94, 134.23, 158.16, 169.28, 169.78; Anal. Calcd for C$_{19}$H$_{19}$NO$_5$: C, 66.85; H, 5.61; N, 4.10. Found: C, 65.92; H, 5.41; N, 3.64.

EXAMPLE 34

(±)-2-(6'-Methoxynaphthyl)propanoyloxysuccinimide (34)

The procedure described in Example 33 was followed with (±)-2-(6'-methoxynaphthyl)propionic acid as the starting material to give the product as a white solid: yield 62%; mp 125.5°–126.5° C.; $^1$H NMR (CDCl$_3$) δ 1.71 (d, 3 H, J=7.2 Hz), 2.76 (br s, 4 H), 3.91 (s, 3 H), 4.19 (q, 1 H, J=7.2 Hz), 7.13 (d, 1 H, J=2.4 Hz), 7.16 (dd, 1 H, J=2.7 Hz, J=8.7 Hz), 7.44 (dd, 1 H, J=1.6 Hz, J=8.6 Hz), 7.74 (d, 1 H, J=8.4 Hz), 7.75 (br s, 1 H), 7.76 (d, 1 H, J=8.1 Hz); $^{13}$C NMR (CDCl$_3$) δ 18.69, 25.32, 42.74, 55.20, 105.68, 119.31, 126.03, 126.51, 127.66, 129.04, 129.56, 133.45, 134.14, 158.15, 169.35, 170.27; Anal. Calcd for C$_{18}$H$_{17}$NO$_5$: C, 66.05; H, 5.23; N, 4.28. Found: C, 65.62; H, 5.29; N, 4.13.

EXAMPLE 35

(±)-2-Phenyl-4-Methylpentanoyloxysuccinimide (35)

The procedure described in Example 33 was followed with 2-phenyl-4-methylpentanoic acid as the starting material to give the product as a cream-colored solid which was recrystallized from ethanol: yield 58%; mp 113.5°–114.5° C.; $^1$H NMR (CDCl$_3$) δ 0.94 (d, 6 H, J=6.6 Hz), 1.51–1.65 (m, 1 H), 1.49 (dd, 1 H, J=7.8 Hz, 6.8 Hz, J$_{gem}$=−13.6 Hz), 2.04 (ddd, 1 H, J=7.8 Hz, 7.4 Hz, J$_{gem}$=−13.6 Hz), 2.74 (br s, 4 H), 3.96 (t, 1 H, J=7.8 Hz), 7.28–7.36 (m, 5 H, ArH); $^{13}$C NMR (CDCl$_3$) δ 21.99, 22.46, 25.47, 42.53, 46.59, 127.75, 127.95, 128.77, 136.88, 168.93, 169.50; Anal. Calcd for C$_{16}$H$_{19}$N$_4$: C, 66.42; H, 6.62; N, 4.84. Found: C, 66.26; H, 6.67; N, 4.66.

EXAMPLE 36

(±)-2-Phenylbutanoyloxyphthalimide (36)

The procedure utilized in Example 1 was followed with N-hydroxyphthalimide substituted for N-hydroxysuccinimide. The product was isolated as a white solid which was recrystallized from ethanol: yield 27%; mp 62°–63° C.; $^1$H NMR (CDCl$_3$) δ 1.04 (t, 3 H, J=7.4 Hz), 1.88–2.03 (m, 1 H), 2.17–2.22 (m, 1 H), 3.86 (t, 1 H, J=7.6 Hz), 7.30–7.43 (m, 5 H), 7.75–7.90 (m 4 H); $^{13}$C NMR (CDCl$_3$ δ 11.61, 27.01, 50.32, 124.05, 128.01, 128.22, 129.00, 129.11, 134.90, 137.02, 162.15, 170.63; Anal. Calcd for C$_{18}$H$_{15}$NO$_4$: C, 69.89; H, 4.87; N, 4.53. Found: C, 69.14; H, 5.04; N, 4.11.

As indicated earlier, the present compounds possess HLE inhibiting activity which indicates that these compounds would be useful in the treatment of such diseases as emphysema, arthritis, artheriosclerosis or the like. For such uses, the compounds would be administered by the usual route, e.g. orally, intravenously, subcutaneously, intraperitoneally or intramuscularly. For emphysema, the compounds would be administered in therapeutically effective amounts, usually orally or rectally, or as a mist for bronchial inhalation.

The amount of compound used to inhibit HLE will vary with the compound selected for use and the nature and extent of the condition involved. It is contemplated, for example, that mists containing from 0.05 to 20% of the active compound with dosages in the order of 2–100 mg per dosage unit several times a day would provide a therapeutically effective amount for the treatment of emphysema. Variations and adjustments in the size and frequency of administration can be determined to provide the desired HLE inhibition.

Pharmaceutical compositions containing the active compounds of the invention may comprise tablets, capsules, solutions or suspensions with conventional non-toxic pharmaceutically acceptable carriers. These compositions may include the usual types of additives, e.g. disintegrating or suspending agents or the like. Compounds selected for intravenous use should be soluble in aqueous solutions, while those used in, for example, oral formulations need not be water-soluble. Topical applications are also contemplated for use in treatment of, for example, dermatitis and acne.

It will be appreciated that various modifications may be made in the invention described herein. Accordingly, the scope of the invention is defined in the following claims wherein:

What is claimed is:

1. A compound of the formula (I)

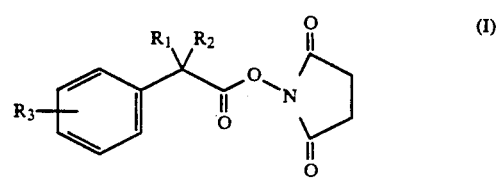

or formula (II)

-continued

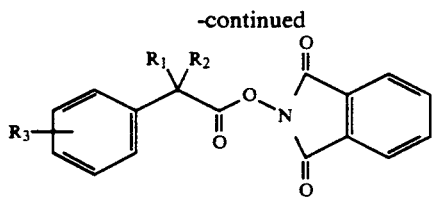

(II)

wherein:
R$_1$ and R$_2$, which may be the same or different, are selected from the group consisting of:
hydrogen, alkyl of 1–6 carbons, cycloalkyl of 3 to 6 carbons or together represent a methylene group —(CH$_2$)$_n$— where n is a whole number from 1 to 5; provided that both R$_1$ and R$_2$ are not hydrogen;

R$_3$ represents one or more substituents up to five selected from the group consisting of:
hydrogen, halogen, haloalkyl of 1–12 carbons, nitro, alkyl of 1–12 carbons, alkoxy of 1–12 carbons, cycloalkyl of 3–12 carbons, alkenyl of 2 to 12 carbons, mono- or dicyclic aryl or a substituent —OCH$_2$O— or —(CH$_2$)$_n$— joining adjacent carbons of the phenyl ring which may be optionally substituted by lower alkyl or lower alkoxy, where n is a whole number from 1 to 5.

2. A compound according to formula (I) wherein one of R$_1$ and R$_2$ is hydrogen and the other is alkyl.

3. A compound according to claim 2 wherein one of R$_1$ and R$_2$ is hydrogen and the other is ethyl.

4. A compound according to claim 2 or claim 3 wherein R$_3$ is hydrogen, lower alkyl, cycloalkyl, lower alkoxy, phenyl or the atoms necessary to complete an optionally substituted ring with the adjacent phenyl.

5. A compound according to claim 1 wherein R$_1$ and R$_2$ are different.

6. A compound according to claim 1 wherein R$_1$ and R$_2$ are the same.

7. A compound according to claim 6 wherein R$_1$ and R$_2$ are both methyl or ethyl or together form a cycloalkyl ring.

8. A compound according to claim 1 of the formula (I) wherein:
R$_1$ is hydrogen or ethyl;
R$_2$ is methyl, ethyl, propyl, butyl or —(CH$_2$)-C(O)CH$_3$ or
R$_1$ and R$_2$ together are (CH$_2$)$_n$ where n is 2, 3 or 4; and
R$_3$ is hydrogen, CF$_3$, CH$_3$, C$_3$H$_4$, OCH$_3$, OC$_2$H$_5$, OC$_4$H$_9$, NO$_2$ or F or
R$_3$ is a group —CHCHC(OCH$_3$)CH— or —OCH$_2$O— joining two adjacent carbons of the phenyl ring.

9. A compound according to claim 1 of the Formula (II) wherein R$_1$ is hydrogen, R$_2$ C$_2$H$_5$ and R$_3$ is hydrogen.

10. A compound according to claim 1 selected from the group consisting of:

(±-2-phenylbutanoyloxysuccinimide;
(R)-(−)-2-phenylbutanoyloxysuccinimide;
(S)-(+)-2-phenylbutanoyloxysuccinimide;
(±)-2-phenylpropanoyloxysuccinimide;
(±)-2-phenylpentanoyloxysuccinimide;
(±)-3-methyl-2-phenylbutanoyloxysuccinimide;
(±)-2-phenylhexanoyloxysuccinimide;
(±)-2-(3'-trifluoromethylphenyl)propanoyloxysuccinimide;
(±)-2-(3'-trifluoromethylphenyl)butanoyloxysuccinimide;
(±)-2-(3'-trifluoromethylphenyl)pentanoyloxysuccinimide;
(±)-3-methyl-2-(3'-trifluoromethylphenyl)butanoyloxysuccinimide;
1-phenylcyclobutanecarboxyloxysuccinimide;
1-phenylcyclopentanecarboxyloxysuccinimide;
(±)-2-(2'-trifluoromethylphenyl)butanoyloxysuccinimide;
(±)-2-(4'-trifluoromethylphenyl)propanoyloxysuccinimide;
(±)-2-(4'-trifluoromethylphenyl)butanoyloxysuccinimide;
(±)-2-(4'-(2-methylpropyl)phenyl)propanoyloxysuccinimide;
(±)-2-(4'-(2-methylpropyl)phenyl)butanoyloxysuccinimide;
2-ethyl-2-phenylbutanoyloxysuccinimide;
(±)-2-(2'-methoxyphenyl)butanoyloxysuccinimide;
(±)-2-(3'-methoxyphenyl)butanoyloxysuccinimide;
(±)-2-(4'-methoxyphenyl)butanoyloxysuccinimide;
(±)-2-(6'-methoxynaphthyl)propanoyloxysuccinimide;
(±)-2-(4'-nitrophenyl)propanoyloxysuccinimide;
(±)-2-(4'-fluorophenyl)propanoyloxysuccinimide;
1-phenylcyclopropanecarboxyloxysuccinimide;
(±)-2-phenyllevulinyloxysuccinimide;
(±)-2-(2'-methylphenyl)-3-methylbutanoyloxysuccinimide;
(±)-2-(3',4'-methylenedioxyphenyl)butanoyloxysuccinimide;
(±)-2(3',4',5'-trimethoxyphenol)butanoyloxysuccinimide;
(±)-2-(4'-ethoxyphenyl)butanoyloxysuccinimide;
(±2-(4'-n-butoxyphenyl)butanoyloxysuccinimide;
(±)-2-(6'-methoxynaphthyl)butanoyloxysuccinimide;
(±)-2-(6'-methoxynaphthyl)propanoyloxysuccinimide:
(±)-2-Phenyl-4-methylpentanoyloxysuccinimide; and
(±)-2-Phenylbutanoyloxyphthalimide.

11. A method of inhibiting HLE in a host in need of such inhibition which comprises administering to said host, an effective amount of a compound according to claim 1.

12. A pharmaceutical composition comprising a compound according to claim 1 and a pharmaceutically acceptable carrier therefor.

* * * * *